United States Patent [19]

Vaughn et al.

[11] Patent Number: 5,334,619

[45] Date of Patent: Aug. 2, 1994

[54] INHIBITION OF POSTHARVEST FRUIT DECAY BY 2-NONANONE

[75] Inventors: Steven F. Vaughn, Peoria; Gayland F. Spencer, Metamora, both of Ill.

[73] Assignee: The United States of America as represented by the Secretary of Agriculture, Washington, D.C.

[21] Appl. No.: 88,470

[22] Filed: Jul. 7, 1993

[51] Int. Cl.$^5$ ............................................. A01N 35/00
[52] U.S. Cl. ................................................... 514/675
[58] Field of Search ......................................... 514/675

[56] References Cited

U.S. PATENT DOCUMENTS 2,283,471  5/1942  Swaine ............................. 514/675
3,474,176  10/1969  Freeman ........................... 514/675

FOREIGN PATENT DOCUMENTS 1212956  3/1960  France ................................ 514/675

OTHER PUBLICATIONS

Nobuyuki Kurita et al., "Antifungal Activity of Components of Essential Oils," Agric. Biol. Chem. 45(4): 945–952 (1981).

Charles L. Wilson et al., "Fruit Volatiles Inhibitory of *Monilinia fructicola* and *Botrytis cinerea*," Plant Disease 71(4): 316–319 (Apr. 1987).

Paul L. Davis et al., "Germination of *Penicillium digitatum* Spores as Affected by Solutions of Volatile Components of Citrus Fruits," Phytopathological Notes 00:488–489 (Apr. 1972).

Peter Schreier, "Quantitative Composition of Volatile Constituents in Cultivated Strawberries, *Fragaria ananassa* cv. Senga Sengana, Senga Litessa and Senga Gourmella," J. Sci. Food Agric. 31:487–494 (1980).

Tapani Pyysalo et al., "Volatiles of Wild Strawberries, *Fragaria vesca* L., Compared to Those of Cultivated Berries, Fragaria x *ananassa* cv. Senga Sengana," J. agric. Food Chem. 27(1): 19–22 (1979).

Tapani Pyysalo, "Identification of Volatile Compounds in Hybrids Between Raspberry (*Rubus idaeus*, L.) and Arctic Bramble (*Rubus arcticus*, L.)," Z. Lebensm. Unters.-Forsch. 162: 263–272 (1976).

Fulgentius N. Lugemwa et al., "Volatiles of Wild Blueberry, *Vaccinium angustifolium:* Possible Attractants for the Blueberry Maggot Fruit Fly, *Rhagoletis mendax*," J. Agric. Food Chem. 37(1): 232–233 (1989).

*Primary Examiner*—Allen J. Robinson
*Attorney, Agent, or Firm*—M. Howard Silverstein; John D. Fado; Curtis P. Ribando

[57] ABSTRACT

The compound 2-nonanone is useful as an antifungal agent against decay organism of berries and other small fruit, particularly those which are susceptible to microbial attact under storage conditions by *Alternaria alternata, Botrytis cinerea* and *Colletotrichum* spp. In a preferred embodiment of the invention, an effective antifungal amount of volatilized 2-nonanone is delivered to the headspace of fruit packaged for market and the vapor is maintained until the package is opened by the consumer.

6 Claims, No Drawings

INHIBITION OF POSTHARVEST FRUIT DECAY BY 2-NONANONE

BACKGROUND OF THE INVENTION

1. Field of the Invention

Fresh market availability of small fruits such as raspberries (*Rubus idaeus* L.) and strawberries (*Fragaria ananassa*, Duchesne) is restricted due to rapid deterioration, primarily the result of fruit senescence and diseases after harvest. Several methods for prolonging shelf-life have been used, including harvesting at earlier stages of maturity than are ideal for consumption (T. M. Sjulin et al., 1987, J. Amer. Soc. Hort. Sci. 112(3: 481–487); gamma irradiation (P. Thomas, 1986, CRC Crit. Rev. Food Sci. Nutrit. 24: 357–400); controlled atmospheres and temperatures (B. L. Goulart et al., 1992, J. Amer. Hort. Sci. 117(2): 265–270; N. F. Sommer, 1985, Can. J. Plant Pathol. 7(4): 331–339); and biological control (W. Janisiewicz, 1988,"Biological Control of Diseases of Fruit," In Biocontrol of Plant Diseases, Vol. 2, K. G. Mukerji and K. L. Garg (ed.), pages 153–165, CRC Press, Boca Raton, Fla.).

This invention relates to a method of using a natural compound, released during ripening by certain fruits, for the postharvest control of fungal decay in small fruit and berries.

2. Description of the Prior Art

Gamma radiation has been examined for use in the extension of the shelf life of perishable fruits (Thomas, supra, 1986). Two major obstacles in the widespread commercial use of gamma radiation to treat perishable fruit have been lack of consumer acceptance and damage to fruit at dosage levels sufficient to effectively control pathogens. Additionally, irradiated foods have been shown to contain and/or release a myriad of radiolytic products, many of which have high mammalian toxicities or contribute to off-flavors (W. W. Nawar, 1986, Food Rev. Int. 2(1): 45–78). Modified atmosphere packaging (MAP) using plastic films decreased strawberry fruit decay but contribute to off-odors and flavors (M. Shamaila et al., 1992, J. Food Sci. 57(5): 1168–1172, 1184). Shamaila et al. found that unpackaged strawberries had the highest overall levels of desirable sensory attributes at all storage times tested, but the berries were infected with fungi (species unreported) after 6 days. Therefore, it would seem that if normal $O_2$ and $CO_2$ levels could be maintained while fungal growth was being prevented, optimum sensory qualities would be preserved.

The principal method of controlling postharvest diseases of these fruit is via the suppression of inoculum production and subsequent infection of the flowers and developing fruit (J. W. Eckert et al., 1988, Ann. Rev. Phytopathol. 26: 433–469). Several fungal species (including *Alternaria alternata*, *Botrytis cinerea* and Colletotrichum spp.) constitute the majority of postharvest pathogens on small fruit and berries (Eckert et al., supra).

Preharvest applications of fungicides have been used to control postharvest fungal decay (J. A. Freeman et al., 1977, Can. J. Plant. Sci. 57(1): 75–80); however, the use of certain fungicides to control grey mold caused by *B. cinerea* has increased the frequency of diseases caused by Mucor spp. and *Rhizopus stolonifer* (Eckert et al., supra). Additionally, strains of *B. cinerea* have developed resistance to several different classes of fungicides (Eckert et al., supra; R. J. Vali et al., 1992, Plant Dis. 76(9): 919–924). The potential for postharvest application of fungicides is limited by both adverse effects due to wetting of the fruit and by stringent federal and state regulations concerning the use of currently-available fungicides (Eckert et al., supra, 1988).

Red raspberries and strawberries release a myriad of volatile compounds during ripening (T. Hirvi, 1983, Lebensm.-Wiss. u.-Technol 16(3): 157–161; T. Hirvi et al., 1982, Z. Lebensm. Unters. Forsch. 175(1): 113–116; E. Honkanen et al., 1980, Z. Lebensm. Unters. Forsch. 171(2): 180–182; M. Larsen et al., 1990, Z. Lebensm. Unters. Forsch. 191(21): 129–131; T. Pyysalo, 1976, Z. Lebensm. Unters. Forsch. 162(3): 263–272; T. Pyysalo et al., 1979, J. Agr. Food Chem 27(1): 19–22). Many of these compounds have been shown to have antifungal activities (N. Fries, 1973, Trans. Brit. Mycol. Soc. 60(1): 1–21; A. Paull et al., 1987, Z. Lebensm. Unters. Forsch. 185(1): 10–13; R. S. Farag et al., 1989, J. Food Sci. 54(11): 74–76; H. Hitokoto et al., 1980, Appl. Environ. Microbiol. 39(4): 818–822; C. L. Wilson et al., 1987, Plant Dis. 71(4): 316–319). Volatile $C_5$-$C_9$ aldehydes occurring in mature citrus fruit were found to inhibit *Penicillium digitatum* (P. L. Davis et al., 1972, Phytopathology 62: 488–489). The natural volatile benzaldehyde has been reported to protect peaches from Rhizopus rot (C. L. Wilson et al, 1989, Ann. Rev. Phytopathol. 27: 425–441). Acetaldehyde vapor has been shown to decrease decay in raspberries and strawberries (E. Pesis et al., 1990, J. Sci. Food Agric. 52: 377–385; K. Prasad et al., 1973, Plant Disease Reporter 57: 795–797; K. Prasad et al., 1974, Phytopathology 64: 948–951). Although many of these compounds are effective fungal inhibitors at relatively low concentrations, at present none are used commercially to prevent or delay fruit decay. These natural volatile compounds may function as effective antifungal agents if sufficient concentrations can be maintained in the gas headspace surrounding the fruit.

SUMMARY OF THE INVENTION

We have now discovered that the volatile compound, 2-nonanone, is useful for inhibiting postharvest decay on small fruit and berries. This compound is particularly useful for inhibiting fungal growth when released at a controlled rate in the headspace of packaging containers used for shipping and marketing the fruit.

In accordance with this discovery, it is an objective of the invention to provide a naturally-occurring agent associated with the ripening of fruit and berries for use in controlling postharvest decay fungi.

It is another object of the invention to provide an antifungal agent characterized by low mammalian toxicity, desirable sensory attributes, resistance to rapid decomposition, a low impartation of damage to fruit, environmental acceptability and high potential to commercial development.

A further object of the invention is to identify 2-nonanone as an agent effective in controlling *Alternaria alternata*, *Botrytis cinerea*, and *Colletotrichum gloeosporioides* on fruit and berries, particularly during postharvest storage and distribution.

Other objects and advantages of the invention will become readily apparent from the ensuing description.

DETAILED DESCRIPTION OF THE INVENTION

The 2-nonanone compound of this invention is characterized by the following structural formula:

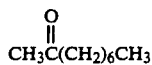

$$CH_3C(CH_2)_6CH_3$$

It exists as a colorless liquid and has a boiling point of approximately 195° C. Other characteristics include: low mammalian toxicity (oral rat $LD_{50}$, 3200 mg/kg) (Lewis, 1978); a pleasant, fruity/floral odor; resistance to rapid decomposition; and sufficient volatility for generating an effective antifungal amount of the compound in the headspace of a storage or packaging container under normal environmental conditions for handling fruit.

The expression "effective antifungal amount", or variations thereof, is used herein to mean that amount of 2-nonanone which inhibits, at a significant level relative to an untreated control, the propagation and/or growth of fungal species which are normally responsible for decay of berries and other small fruit during storage and marketing. Especially preferred is that amount which will completely inhibit fungal growth (as manifest by the spread of mycelia) under normal conditions for storing or packaging fruit, without causing necrotic tissue damage to the fruit. In general, it is desirable to maintain a vapor phase concentration of the nonanone in the range of about 0.01 to about 0.05 μL/ml, and preferably a concentration in the range of about 0.02 to about 0.20 μL/ml. Most preferred is a concentration in the range of about 0.05 to about 0.15 μL/ml. The actual target concentration for treatment will of course depend upon the particular fruit being treated, the species of fungus to be controlled and the conditions under which decay is to be inhibited.

Contemplated for treatment herein are small fruits, particularly berries. Berries of commercial interest which are most susceptible to postharvest fungal decay are raspberries and strawberries. Of course other fruits of interest include blueberries, blackberries, hackberries, gooseberries, and boysenberries. As previously mentioned, the most common decay fungi of these berries are *Alternaria alternata, Botrytis cinerea* and *Colletotrichum* spp.

Although an efficacious mode of treatment would be to contact the fruit with the liquid 2-nonanone, residual agent on the fruit surface might adversely influence consumer acceptance. Therefore, it is preferred to apply the nonanone as a vapor. This is most directly achieved by causing the compound to volatilize into the atmosphere adjacent to the surrounding fruit. For example, in bulk storage, air can be passed over a remote source of the liquid compound and circulated around the fruit. Alternatively, the compound may be incorporated into a slow release vehicle or carrier, such as by encapsulation or placement in a closed permeable container. Another approach is impregnation of the nonanone into the packaging container itself.

In a preferred embodiment for controlled release, the 2-nonanone is formulated with a pregelatinized starch as a carrier. The release rate of the agent from the starch can be tailored by the addition of a retarding agent, such as glycerine. The formulation comprising the agent and carrier is then loaded into a tube. Appropriate preselection of the tube diameter serves as an additional mechanism for controlling the release rate. As a final step, the tube is wrapped in a film permeable to the 2-nonanone. The resultant delivery system finds particular application in situations where direct contact between the liquid form of the nonanone and the fruit is to be absolutely avoided.

The following examples are intended only to further illustrate the invention and are not intended to limit the scope of the invention which is defined by the claims.

EXAMPLE 1

Fungal Cultures

Fungal cultures of *A. alternata* and *B. cinerea* were obtained from the Agricultural Research Service, NRRL Culture Collection in Peoria, Ill. These cultures exhibited positive pathogenicity on healthy raspberries and strawberries. An isolate of *C. gloeosporioides* pathogenic on blueberries was obtained from the USDA-/ARS Cranberry and Blueberry Research Center, Chatsworth, N.J. All cultures were maintained at 24° C. and 95% relative humidity on V-8 juice agar supplemented with 0.3% $CaCO_3$ and adjusted to pH 5.8. Spores of each fungus were removed from sporulating cultures by carefully brushing the surface of the media with a glass rod and suspending the spores in sterile water. The concentrations of spores in the suspensions were adjusted to concentrations of $10^6$ to $10^7$ spores/ml. These suspensions were mixed together to form a composite suspension which was used to inoculate all the fruit in a given experiment.

Fruit

Untreated red raspberries (cv. 'Heritage') and strawberries (cv. 'Ozark Beauty') were harvested and used the same day. Berries were selected on the basis of uniform size, color, firmness, and absence of evidence of defects or diseases.

Bioassay System

A bioassay system was developed to test the effects of the volatile compounds on fungal growth both on intact fruit and on V-8 juice medium. The apparatus consisted of 75 ml glass jars into which either fruit or sterilized V-8 juice medium (10 ml) were added. These jars were placed in 275 ml airtight glass jars with aluminum foil cap liners. The bottom of each 275 ml jar was fitted with a 5.5 cm filter paper disk (Whatman No. 1) for application of the appropriate amount of test compound. The total gas headspace in the larger jars after the addition of all components was 250 ml.

Treatment of Inoculated Fruit With Volatiles

Fifteen compounds reported as major volatile components of red raspberries and/or strawberries and representing a variety of chemical classes were evaluated for suppression of fungi growing directly on the fruit. These compounds included two aldehydes, seven alcohols, three ketones, one ester and one heterocycle containing both an alcohol and ketone moiety. The test compounds were selected on the basis of a preliminary screening for suitable volatility, low mammalian toxicity, and commercial availability. All chemicals tested were obtained from the supplier (Aldrich Chem. Co., Milwaukee, Wis.) and used without further modification.

Red raspberries and strawberries were rinsed with sterile distilled water and allowed to dry before inoculation. The fruit was sprayed with the spore suspension to runoff. Single red raspberries or strawberries were placed in the 75 ml jars, and 100 μl each of a single test compound was added to the filter paper on the bottom of a 275 ml jar. The 275 ml jar was then sealed. Fruit were kept at 10° C. in the dark for 10 days then rated for development of fungi and for damage to the fruit due to the treatments. Categories based on percentage of the fruit surface area visibly covered with fungi were: 0, no detectable fungal growth; 1, 0–25% of the fruit covered with mycelia; 2, 25–75% of the fruit covered with mycelia; and 3, >75% of the fruit covered with mycelia. Fruit damage rating catagories were: 0, no detectable damage; 1, some surface damage; 2, moderate fruit damage with fluid loss; and 3, extensive necrosis and heavy fluid loss. Each treatment was replicated five times and the experiment was repeated.

Effect of Volatiles on Inoculated Fruit

Of the fifteen volatile compounds tested, five completely suppressed fungal growth on both raspberry and strawberry fruit; three of these five did not cause extensive tissue necrosis damage of the fruit. Of these three compounds, 2-nonanone was selected for further study. The results of fungal growth inhibition and fruit damage assessment are reported in Table I, below. As results from both experiments were similar, only results from one experiment are reported.

EXAMPLE 2

Treatment of Isolated Cultures With 2-Nonanone Vapor

The 2-nonanone was tested to determine threshold levels required to completely inhibit isolated fungal cultures growing on V-8 juice medium. The fungi assayed against included B. cinerea, C. gloeosporioides and A. alternata. The compound was bioassayed as a volatile using the apparatus described in Example 1 by placing 7 mm diameter plugs of mycelia from actively-growing 1 week-old cultures on V-8 juice media in the 75 ml jars, with the appropriate amount (0, 5, 10, 25 or 100 μl) of compound applied to the filter paper on the bottom of the larger jar. Assuming complete volatilization, these amounts would produce a nonanone concentration within the headspace of 0.02, 0.04, 0.10, and 0.40 μL/ml, respectively. The sealed jars were then placed in a growth chamber in the dark at 10° C. for 7 days. Due to growth of fungi limited to the plug in many cases and the difficulty of accurately measuring the fungal growth in the jars, a rating system was developed as follows: 0, no growth of fungi, including on plug; 1, growth on plug only; 2, small amount of fungal growth on medium; 3, most of medium covered with fungal mycelia; and 4, all of medium covered. The treatment was replicated three times and the data were treated by statistical analysis of variance. The results are reported in Table II, below.

EXAMPLE 3

Treatment of Isolated Cultures With 2-Nonanone in the Growth Medium

2-Nonanone was assayed as a medium component by adding an appropriate amount to cooled V-8 juice media in 9.0 cm plastic petri dishes. Experiments were initiated by placing 7 mm plugs of mycelia in the center of the petri dishes. As the cultures were nearly circular, the radii (from the inoculum plug to one typical point on the growing margin) of the cultures were measured and expressed as a percentage of the control. The treatment was replicated five times and the data were treated by analysis of variance. The results are reported in Table III, below. It is apparent from these data that when the 2-nonanone is added directly to the medium, it is less inhibitory than when allowed to volatize in the headspace.

EXAMPLE 4

Starch Carrier Delivery System

A fast release formulation was prepared by thoroughly mixing 5 g of 2-nonanone with 15 g "Miragel" (pregelatinized cornstarch, A. E. Staley, Decatur, Ill.). Also, a slow release formulation was made by mixing 15 g "Miragel" with 2.5 g glycerine followed by 5 g of 2-nonanone. The resultant mixtures were packed into glass tubes (0.5 cm × 2.0 cm) and heat-sealed in polypropylene plastic bags (polypropylene allows vapor phase 2-nonanone to pass and be detected by gas chromatography; data not presented). Single tubes were placed in airtight 2.45 L dessicator flasks which were fitted with a septa allowing headspace gas samples to be removed.

Headspace Gas Analysis

Gas headspace samples (1 ml) were collected with a 1 ml gastight syringe (Dynatech Precision Sampling Co., Baton Rouge, La.) and were analyzed by a Hewlett Packard Model 5890 gas chromatograph (Hewlett-Packard Co., Palo Alto, Calif.) using a capillary column (15 m × 0.25 nun) coated with a 0.25 μm film (DB-1; J&W Scientific, Folsom, Calif.). Helium gas carrier flow through the column was 1 ml/min and the sample was injected into an 100/1 inlet splitter (total flow 100 ml/min). The injection temperature was set at 180° C., the flame ionization detector was set at 290° C. and the oven was run isothermally at 75° C. Peak areas were quantified by comparison to a standard curve prepared from the response of a range of dilutions of known concentrations of 2-nonanone in hexane.

Treatment of Berries With 2-Nonanone Using Starch Carrier Delivery System

The results from storing red raspberries and strawberries in airtight containers for one week at 10° C. with both the slow and fast release formulations described above are shown in Table IV. Although the fast release formulation had a higher level of 2-nonanone after 24 hours, both treatments contained the same headspace concentration after 7 days. The treated berries lacked any visible fungi, and lacked significant fruit damage, although fruit had a slight odor of 2-nonanone when first removed from the flasks. The berries had little off-flavor as judged by informal lab bench screening.

It is understood that the foregoing detailed description is given merely by way of illustration and that modification and variations may be made therein without departing from the spirit and scope of the invention.

TABLE I

Fungal growth and fruit damage ratings of inoculated raspberry and strawberry fruit after 10 days exposure to 0.4 μl/ml volatile compounds

| Treatment | Fungal Rating[x] | | Fruit damage rating[y] | |
|---|---|---|---|---|
| | Raspberry | Strawberry | Raspberry | Strawberry |

TABLE I-continued

| | | | | |
|---|---|---|---|---|
| Control | 2.4 a[z] | 3.0 a | 2.0 a | 2.7 a |
| 2-Nonanone | 0.0 b | 0.0 b | 2.0 a | 1.7 b |

[x]Mean of fungal growth, 0 = no fungi present, 3 = fruit completely covered by fungal mycelia.
[y]Mean of fruit damage, 0 = intact, undamaged fruit, 3 = whole fruit necrotic and watersoaked.
[z]Mean separation among all values by Duncan's multiple range test, $p < 0.05$. Values in a column followed by different letters are significantly different.

TABLE II

Response of three fungal species to vapor phase concentrations of volatile odor compounds

| Treatment | Fungal Growth Rating[x] | | |
|---|---|---|---|
| μL/mL | A. alternata | B. cinerea | C. gloeosporioides |
| Control | 4.0 a[y] | 4.0 a | 4.0 a |
| 2-Nonanone | | | |
| 0.02 μl/ml | 2.7 b | 1.0 b | 2.0 b |
| 0.04 μl/ml | 1.3 c | 0.0 c | 0.6 c |
| 0.10 μl/ml | 0.0 d | 0.0 c | 0.0 c |
| 0.40 μl/ml | 0.0 d | 0.0 c | 0.0 c |

[x]Mean of fungal growth, 0 = no growth, 4 = media completely covered.
[y]Mean separation among all values by Duncan's multiple range test, $p < 0.05$. Values in a column followed by different letters are significantly different.

TABLE III

Radial growth of fungal cultures on media with added volatile compounds

| | Fungal Growth (% of control)[x] | | |
|---|---|---|---|
| Treatment (%) | A. alternata | B. cinerea | C. gloeosporioides |
| 2-Nonanone | | | |
| 0.01% | 85.2 a | 100.0 a | 100.4 a |
| 0.10% | 48.7 b | 83.0 b | 95.7 a |
| 1.00% | 0.0 c | 0.0 c | 0.0 b |

[x]Mean separation among all values by Duncan's multiple range test, $p < 0.05$. Values in a column followed by different letters are significantly different.

TABLE IV

Response of raspberry and strawberry fruit after exposure to 2-nonanone from delivery system for 7 days at 10° C.

| | Headspace concentration (μg/ml) | Fruit Damage Rating[x] | |
|---|---|---|---|
| Treatment | of 2-nonanone ± S.E. | Raspberry | Strawberry |
| Control (7 days) | 0.00 ± 0.00 | 2.3 a[y] | 2.5 a |
| Slow release (24 hours) | 0.04 ± 0.01 | 0.0 b | 0.0 b |
| Fast release (24 hours) | 0.11 ± 0.02 | 0.2 b | 0.0 b |
| Slow release (7 days) | 0.13 ± 0.01 | 0.4 b | 0.0 b |
| Fast release (7 days) | 0.13 ± 0.00 | 0.4 b | 0.0 b |

[x]Mean of fruit damage, 0 = intact, undamaged fruit, 3 = fruit completely necrotic and water-soaked.
[y]Mean separation among all values by Duncan's multiple range test, $p < 0.05$. Values in a column followed by different letters are significantly different.

I claim:

1. A method of inhibiting fungal decay in a fruit comprising contacting said fruit with effective fungicidal amount of the compound 2-nonanone.

2. The method of claim 1 wherein said fruit is a berry.

3. The method of claim 2 wherein said berry is selected from the group consisting of strawberry, raspberry, blueberry, blackberry, hackberry, gooseberry, and boysenberry.

4. The method of claim 1 wherein said 2-nonanone is vaporized.

5. The method of claim 1 wherein said fruit is harvested fruit.

6. The method of claim 5 wherein said harvested fruit is stored in a closed container and is contacted with vaporized 2-nonanone.

* * * * *